United States Patent [19]

Higuchi et al.

[11] Patent Number: 4,757,083
[45] Date of Patent: Jul. 12, 1988

[54] NOVEL PYRROLIDINYLAMIDE ESTER DERIVATIVES HAVING ANTI-PROLYL ENDOPEPTIDASE ACTIVITY AND SYNTHESIS AND USE THEREOF

[75] Inventors: Naoki Higuchi; Masayuki Saitoh; Masaki Hashimoto, all of Osaka; Harukazu Fukami, Kyoto; Takaharu Tanaka, Osaka, all of Japan

[73] Assignee: Suntory Limited, Osaka, Japan

[21] Appl. No.: 936,445

[22] Filed: Dec. 1, 1986

[30] Foreign Application Priority Data

Nov. 29, 1985 [JP] Japan ................. 60-268994

[51] Int. Cl.⁴ ............... A61K 31/40; C07D 295/18
[52] U.S. Cl. ............................ 514/423; 548/540
[58] Field of Search ..................... 548/540; 514/423

[56] References Cited

U.S. PATENT DOCUMENTS

| | | | |
|---|---|---|---|
| 2,956,064 | 10/1960 | Kagan et al. | 549/267 |
| 3,801,636 | 4/1974 | Horrom | 548/540 X |
| 4,206,122 | 6/1980 | Natarajan et al. | 548/540 X |
| 4,334,073 | 6/1982 | Diehr | 548/540 X |
| 4,510,142 | 4/1985 | Cousse et al. | 514/255 |

FOREIGN PATENT DOCUMENTS

| | | |
|---|---|---|
| 0077720 | 4/1983 | European Pat. Off. |
| 188317 | 9/1985 | Japan . |
| 172929 | 9/1985 | Japan . |

OTHER PUBLICATIONS

Noller, "Chemistry of Organic Compounds", 3rd. ed. (1965), pp. 189,190,193.
Chemical Abstracts, vol. 90, No. 3 "N-(Substituted Aminoalkyl)-2-oxo-1-pyrrolidine acetamides" Jan. 15, 1979; 90:22798b; L'Italien et al.
The proceedings of the 1984 Annual Meeting of "The Agricultural Chemical Society of Japan", pp. 752–754.
Agric. Biol. Chem., 42(12), 2417–2419, (1978); Yoshimoto et al.

*Primary Examiner*—Joseph Paul Brust
*Attorney, Agent, or Firm*—Cushman, Darby & Cushman

[57] ABSTRACT

A novel pyrrolidinylamide ester derivative that exhibits inhibitory activity against prolyl endopeptidase, methods for synthesis thereof and its use as an inhibitor against said enzyme are disclosed. The pyrrolidinylamide ester of the invention has the following general formula:

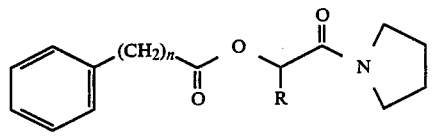

wherein n is 0 or an integer of 1 to 7 and R is hydrogen atom or a straight or branched alkyl having 1 to 8 carbon atoms.

5 Claims, No Drawings

NOVEL PYRROLIDINYLAMIDE ESTER DERIVATIVES HAVING ANTI-PROLYL ENDOPEPTIDASE ACTIVITY AND SYNTHESIS AND USE THEREOF

BACKGROUND OF THE INVENTION

1. Field of the Invention

The present invention relates to a novel compound that exhibits enzyme inhibitory activity against prolyl endopeptidase (EC. 3.4.21.26). The invention also relates to a method for chemical synthesis of such novel compounds, as well as a prolyl endopeptidase activity inhibitor that contains said compound as the active ingredient.

Prolyl endopeptidase is known to inactivate neurotransmitters such as substance P, thyrotropin-releasing hormone (TRH) and neurotensin, or vasopressin speculatively associated with memory. Tsuru and Yoshimoto of the Department of Pharmaceutical Sciences, Nagasaki University, found that compounds capable of inhibiting prolyl endopeptidase activity were effective in preventing experimental amnesia caused in rats by scopolamine. Based on this discovery, they suggested the potential use of anti-prolyl endopeptidase substances as anti-amnesic agents.

Motivated by the report of Tsuru and Yoshimoto, the present inventors have made various efforts to find novel compounds that exhibit strong inhibitory activity against prolyl endopeptidase as an anti-amnesic activity and which yet display satisfactorily low toxicity levels.

2. Prior Art

U.S. patent applications Ser. No. 760,411 (filed on July 30, 1985), Ser. No. 852,709 (filed on Apr. 16, 1986), Ser. No. 852,710 (filed on Apr. 16, 1986) and Ser. No. 852,711 (filed on Apr. 16, 1986), now U.S. Pat. No. 4,701,465 patented Oct. 20, 1987, all of which have been assigned to the assignee of this invention, disclose certain types of compounds which have inhibitory activity against prolyl endopeptidase and are thus effective in treating amnesia.

SUMMARY OF THE INVENTION

The inventors have now found novel compounds having the general formula (I) shown below which exhibit strong inhibitory activity against prolyl endopeptidase while displaying low toxicity and they are thus expected to be effective against amnesia. The compounds of the invention are close to natural substances, being a combination of fatty acids, which enjoy a high safety level as natural compounds, and amino acids or peptide compounds.

DETAILED DESCRIPTION OF THE INVENTION

The pyrrolidinylamide ester derivative having anti-prolyl endopeptidase activity of the present invention is represented by the general formula (I):

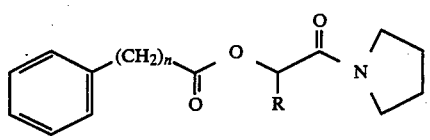

wherein n is 0 or an integer of 1 to 7, preferably 3 to 5, and R is hydrogen atom or a straight or branched alkyl having 1 to 8, preferably 3 to 5, carbon atoms.

The compounds of formula (I) differ greatly from the known anti-amnesic agents of piracetam derivatives in that the former contains a pyrrolidine amide of a hydroxy acid. Because they are derivatives of hydroxy acids, the compounds of the formula (I) present extremely low toxicity levels in organisms.

The following compounds of the formula (I) are particularly preferred because of their high anti-prolyl endopeptidase activities (the following compounds may be sometimes referred to by the numbers given in parentheses hereinafter):

(SUAM 1287)

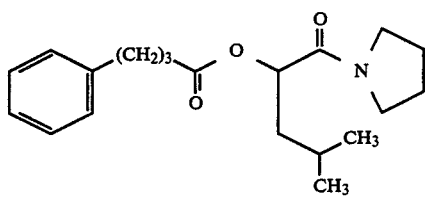

(SUAM 1288)

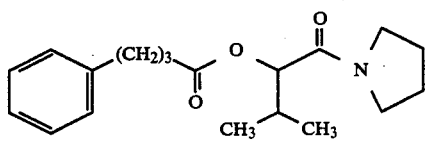

(SUAM 1332)

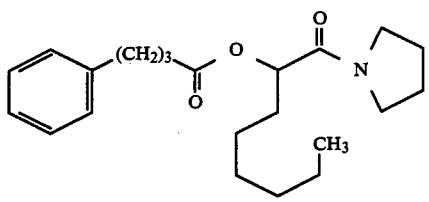

The compounds of the present invention of the formula (I) may also be synthesized by known acylation methods. But the compounds may advantageously be synthesized by the following methods of the invention which will be explained hereunder. The abbreviation "WSCD" as used herein means N-ethyl-N',N'-dimethylaminopropylcarbodiimide.

The intermediate O-acyl hydroxy acid of the formula (II):

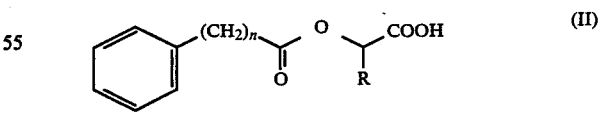

wherein n and R have the meanings given above, may be obtained by reacting an ω-phenylalkyl carbonyl halide of the formula (III):

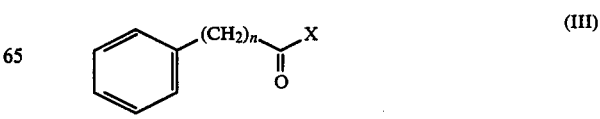

wherein n has the same meaning as given above and X represents a halogen atom, with a hydroxycarboxylic acid of the formula (IV):

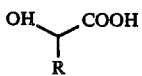  (IV)

wherein R has the same meaning as given above, in the presence of a base. As bases which may be used in this reaction, trialkylamines and aromatic amines etc. can be mentioned. The reaction temperature is preferably below room temperature. The solvent may be selected from those which remain inert in the reaction, such as ether type solvent. Especially preferred is tetrahydrofurane.

The compound of the invention may be obtained from the compound of the formula (II) by condensation of the latter with pyrrolidine under the presence of a condensation agent. Examples of suitable condensation agents are those which are commonly used in peptide synthesis such as N',N'-dicyclohexylcarbodiimide and WSCD, etc. However, the condensation may be conducted by any conventional method such as the acid chloride method.

Alternatively, the compound of the present invention may be obtained from a carbonyl imide of the formula (V):

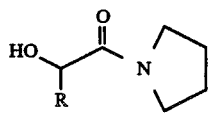 (V)

wherein R has the same meaning as given above, by reacting said compound with an ω-phenylalkyl carbonyl halide of the foregoing formula (III) in the presence of an organic base as mentioned above.

The present invention is hereinunder described in greater detail by way of Examples.

EXAMPLE 1

N-[2-(γ-phenyl)butyryloxy-4-methylvaleryl]pyrrolidine (SUAM 1287)

2-Hydroxy-4-methylvaleric acid (10 mmol) was dissolved in anhydrous tetrahydrofurane (ca. 50 ml), to which triethylamine (10 mmol) was then added. γ-Phenylbutyryl chloride (10 mmol) and then triethylamine (10 mmol) were slowly added dropwise to the resulting solution under cooling with ice. The mixture was allowed to return to room temperature and then stirred throughout one whole day and night.

After the reaction, the hydrochloride salt of triethylamine which had precipitated was removed by filtration. The resultant solution in tetrahydrofurane was distilled off in vacuo to obtain the residue which was then dissolved in ethyl acetate and the solution was washed twice with 1N hydrochloric acid. The organic layer was dried over anhydrous magnesium sulfate, the solvent was distilled off under vacuum and the resulting residue was purified by medium pressure column chromatography on silica gel. The resulting 2-(γ-phenyl)-butyryloxy-4-methylvaleric acid was dissolved in dry methylene chloride (100 ml) together with pyrrolidine (1 equivalent). WSCD (1 equivalent) was added thereto and the mixture was stirred throughout one whole day and night. After the completion of the reaction, the mixture was washed successively with 1N hydrochloric acid, saturated brine, saturated aqueous sodium bicarbonate and again saturated brine, in that order, and was then dried over anhydrous magnesium sulfate. The dried mixture was concentrated by distillation under vacuum. The residue was subjected to medium pressure column chromatography on silica gel whereby the titled compound was obtained.

Appearance: colorless oil

IR spectrum (film, $cm^{-1}$): 2950, 2860, 1720, 1650, 1440, 740, 695.

NMR spectrum ($CDCl_3$, δ): 0.96(3H, d, J=3 Hz), 1.00(3H, d, J=3 Hz), 1.20–2.80(13H, m), 3.20–3.90(4H, m), 5.16(1H, dd, J=4, J=9 Hz), 7.20–7.40(5H, m).

EXAMPLE 2

N-[2-(γ-phenyl)butyryloxy-3-methylbutyryl]pyrrolidine (SUAM 1288)

The titled compound was obtained by repeating the process of Example 1 but using 2-hydroxy-3-methylbutyric acid in place of 2-hydroxy-4-methylvaleric acid.

IR spectrum (film, $cm^{-1}$): 2960, 2870, 1720, 1650, 1440, 740, 695.

NMR spectrum ($CDCl_3$, δ): 0.98(3H, d, J=6 Hz), 1.06(3H, d, J=6 Hz), 1.80–2.80(11H, m), 3.30–4.00(4H, m), 4.80(1H, d, J=8 Hz), 7.10–7.40(5H, m).

EXAMPLE 3

N-[2-(γ-phenyl)butyryloxy-n-capryloyl]pyrrolidine (SUAM 1332)

The titled compound was obtained by repeating the process of Example 1 but using 2-hydroxy-n-caprylic acid in place of 2-hydroxy-4-methylvaleric acid.

IR spectrum (film $cm^{-1}$): 2940, 2870, 1730, 1640, 1440, 740, 700.

NMR spectrum ($CDCl_3$, δ): 0.98(3H, m), 1.30(8H, m), 1.60–2.80(12H, m), 3.20–3.80(4H, m), 5.06(1H, dd, J=5, J=8 Hz), 7.10–7.40(5H, m).

EXAMPLE 4

Measurement of anti-prolyl endopeptidase activity

The method of Yoshimoto and Tsuru [T. Yoshimoto and D. Tsuru, Agric. Biol. Chem., 42, 2417 (1978)] was used to measured the anti-prolyl endopeptidase activities of several compounds of the present invention. A mixture of 0.0025M Z-glycyl-proline-β-naphthylamide (0.25 ml), 0.1M phosphate buffer (pH, 7.0; 0.99 ml) and a solution of a particular anti-prolyl endopeptidase compound (0.01 ml) was incubated in a test tube at 37° C. for 3 minutes. Thereafter, 0.1 ml of a solution of prolyl endopeptidase (0.2 U/ml) was added and the mixture was incubated at 35° C. for 10 minutes. After the reaction, 2.0 ml of Triton X-100 in 1M acetate buffer (pH, 4.0) was added to the reaction mixture so that the final concentration of the surfactant was 10%. The mixture was left at room temperature for 15 minutes and the absorbance (a) at 410 nm was measured.

A sample of a blind test was prepared by using the buffer instead of the anti-prolyl endopeptidase compound and its absorbance (b) was also measured. The percent inhibition of prolyl endopeptidase was calculated by the formula:

$[(b-a)/b] \times 100$ and the amount of a specific compound needed to achieve 50% inhibition ($IC_{50}$) was determined. The results are shown in Table 1.

TABLE 1

| Compound (Example No.) | $IC_{50}$ (μg/test tube) |
|---|---|
| 1 | 0.70 |
| 2 | 0.90 |
| 3 | 4.0 |

The compounds of the invention are useful for their anti-prolyl endopeptidase activity in treating patients suffering from amnesia. Therefore, the present invention also relates to a pharmaceutical composition comprising at least one compound of the formula (I) together with a pharmaceutically acceptable carrier.

The formulation of the agent of the invention includes either solid formulations such as capsules, tablets and powders, or liquid formulations such as elixirs, syrups and suspensions for oral administration. Alternatively, the active compounds (I) may be formulated as injections or suppositories.

The carrier included in the agent of the invention may be selected from pulverulent solid carriers such as lactose, saccharose, dextrose, mannitol, sorbitol, cellulose, and glycine etc.

The agent of the invention may further contain a lubricant, a binder or a disintegrator. Examples of suitable lubricants are silicon dioxide, talc, magnesium stearate and polyethylene glycol. Examples of suitable binders are starch, gelatin, tragacanth, methyl cellulose and polyvinyl pyrrolidone. Examples of suitable disintegrators are starch and agar etc.

The active ingredient (I) of the agent of the invention is orally administered to an adult patient in a dose of 10 to 4000 mg, preferably 100 to 1000 mg/day, or administered parenterally in a dose of 1 to 2000 mg, preferably 50 to 500 mg/day. The dose may be varied depending on the disease, age, weight, or condition of the patient and the formulation of the drugs.

Formulation 1

| Ingredient | Part |
|---|---|
| Compound of the formula (I) | 45 |
| Starch | 15 |
| Lactose | 40 |

The ingredients are mixed thoroughly, and tablets or capsules are formulated from the mixture.

Formulation 2

| Ingredient | Part |
|---|---|
| Compound of the formula (I) | 10 |
| Lactose | 75 |
| Magnesium oxide (MgO >96%) | 15 |

The above ingredients are mixed thoroughly, and powders or fine granules are formed from the mixture.

Formulation 3

| Ingredient | Part |
|---|---|
| Compound of the formula (I) | 1 |
| Surface active agent | 5 |
| Physiological saline | 94 |

The above ingredients are mixed under warming, and dispensed under sterile conditions into ampoules for use as injections.

What is claimed is:

1. A pyrrolidinylamide ester derivative of the formula:

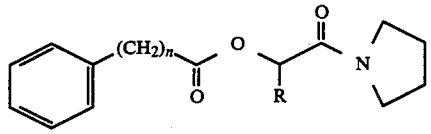

wherein n is an integer of 3 to 5 and R is a straight or branched alkyl having 3 to 6 carbon atoms.

2. A compound according to claim 1 wherein n is an integer of 3.

3. A compound according to claim 1 wherein R is a straight or branched alkyl having 3 to 5 carbon atoms.

4. A compound according to claim 1 which is expressed by the following formula:

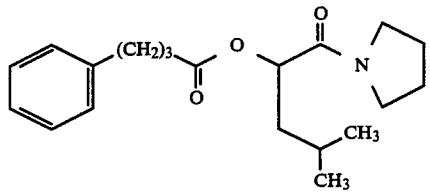

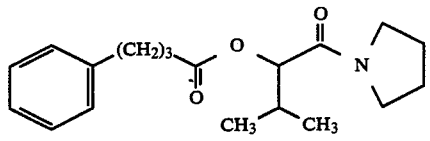

or

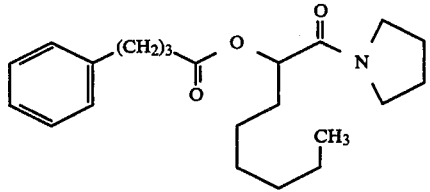

5. A pharmaceutical composition comprising a prolyl endopeptidase inhibiting amount of a compound of the formula:

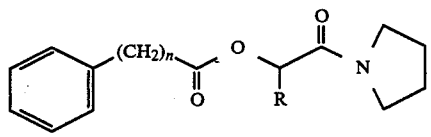

wherein n is an integer of 3 to 5 and R is a straight or branched alkyl having 3 to 6 carbon atoms, together with a pharmaceutically acceptable carrier.

* * * * *